US008999353B2

(12) United States Patent
Pearse et al.

(10) Patent No.: US 8,999,353 B2
(45) Date of Patent: Apr. 7, 2015

(54) METHOD OF ELICITING AN IMMUNE RESPONSE AGAINST PANDEMIC INFLUENZA VIRUS

(75) Inventors: Martin Pearse, Victoria (AU); Steve Rockman, Victoria (AU); David Ryan, Victoria (AU)

(73) Assignee: CSL Limited, Parkville, Victoria (AU)

(*) Notice: Subject to any disclaimer, the term of this patent is extended or adjusted under 35 U.S.C. 154(b) by 459 days.

(21) Appl. No.: 12/679,654

(22) PCT Filed: Oct. 9, 2008

(86) PCT No.: PCT/AU2008/001500

§ 371 (c)(1), (2), (4) Date: Jun. 28, 2010

(87) PCT Pub. No.: WO2009/046497

PCT Pub. Date: Apr. 16, 2009

(65) Prior Publication Data

US 2010/0291146 A1 Nov. 18, 2010

Related U.S. Application Data

(60) Provisional application No. 60/979,572, filed on Oct. 12, 2007.

(51) Int. Cl.

*A61K 39/145* (2006.01)
*A61K 39/00* (2006.01)

(52) U.S. Cl.

CPC ..... *A61K 39/145* (2013.01); *A61K 2039/55572* (2013.01); *A61K 2039/55577* (2013.01); *C12N 2760/16134* (2013.01)

(58) Field of Classification Search

CPC .................. A61K 39/145; A61K 2039/55577; C12N 2760/16134

See application file for complete search history.

(56) References Cited

U.S. PATENT DOCUMENTS

| | | | |
|---|---|---|---|
| 6,518,239 | B1 | 2/2003 | Kuo et al. |
| 7,776,343 | B1 | 8/2010 | Cox et al. |
| 2003/0190333 | A1 | 10/2003 | Mossman et al. |
| 2006/0210555 | A1 | 9/2006 | Kensil et al. |
| 2006/0287263 | A1 | 12/2006 | Davis et al. |
| 2007/0190072 | A1 | 8/2007 | Cebon et al. |
| 2009/0324642 | A1 | 12/2009 | Edwards et al. |
| 2010/0010193 | A1 | 1/2010 | Cox et al. |
| 2010/0047271 | A1 | 2/2010 | Drane et al. |

FOREIGN PATENT DOCUMENTS

| | | | |
|---|---|---|---|
| WO | WO 99/52547 | A1 | 10/1999 |
| WO | WO 01/75096 | A1 | 10/2001 |
| WO | WO 01/95934 | A2 | 12/2001 |
| WO | WO 02/20045 | A2 | 3/2002 |
| WO | WO 2005/070415 | A1 | 8/2005 |
| WO | WO 2005/110379 | A2 | 11/2005 |
| WO | WO 2006/100110 | A1 | 9/2006 |

OTHER PUBLICATIONS

Rimmelzwaan et al (Vaccine 19:1180-1187, 2001).*

Ennis et al (Virology 259:256-261, 1999; in IDS).*

Rimmelzwaan et al (Vaccine 20:158-163, 2001).*

Sandbulte et al., "Cross-Reactive Neuraminidase Antibodies Afford Partial Protection against H5N1 in Mice and Are Present in Unexposed Humans," PLoS Medicine, vol. 4, Issue 2, pp. 265-272, Feb. 2007.

Supplementary European Search Report issued on Dec. 27, 2011 in application No. EP 08 80 0134.

Office Action issued on Feb. 22, 2011 by the Examiner in U.S. Appl. No. 12/439,054 (US 2009/0324642.

Office Action issued on Aug. 25, 2011 by the Examiner in U.S. Appl. No. 12/439,054 (US 2009/0324642.

Office Action issued on Feb. 6, 2012 by the Examiner in U.S. Appl. No. 12/439,054 (US 2009/0324642.

International Search Report issued on Dec. 16, 2008 in application No. PCT/AU2008/001500.

Ennis et al., "Augmentation of Human Influenza A Virus-Specific Cytotoxic T Lymphocyte Memory by Influenza Vaccine and Adjuvanted Carriers (ISCOMS)," *Virology*, vol. 259, pp. 256-261, 1999.

Coulter et al., "Intranasal vaccination with ISCOMATRIX® adjuvanted influenza vaccine," *Vaccine*, vol. 21, pp. 946-949, 2003.

Windon et al., "Local immune responses to influenza antigen are synergistically enhanced by the adjuvant ISCOMATRIX®," *Vaccine*, vol. 20, pp. 490-497, 2001.

Scheerlinck et al., "Local immune responses following nasal delivery of an adjuvanted influenza vaccine," *Vaccine*, vol. 24, pp. 3929-3936, 2006.

Sambhara et al., "Heterosubtypic Immunity against Human Influenza A Viruses, Including Recently Emerged Avian H5 and H9 Viruses, Induced by FLU-ISCOMM Vaccine in Mice Requires both Cytotoxic T-Lymphocyte and Macrophage Function," *Cellular Immunology*, vol. 211, pp. 143-153, 2001.

International Search Report issued on Nov. 2, 2007 in application No. PCT/AU2007/001277.

Alpar et al., "Biodegradable mucoadhesive particulates for nasal and pulmonary antigen and DNA delivery," *Advanced Drug Delivery Reviews*, vol. 57, pp. 411-430, 2005.

Bennett et al., "Aerosolized measles and measles-rubella vaccines induce better measles antibody booster responses than injected vaccines: randomized trials in Mexican schoolchildren," *Bulletin of World Health Organization*, vol. 80, No. 10, pp. 806-812, 2002.

(Continued)

*Primary Examiner* — Mary E Mosher

(74) *Attorney, Agent, or Firm* — Foley & Lardner LLP

(57) ABSTRACT

A method for eliciting or inducing a protective immune response in a subject against a pandemic subtype of influenza virus comprises administering to the subject a composition comprising (i) at least one immunogen of an endemic influenza subtype, and (ii) an immunogen-free immunostimulating complex as adjuvant.

7 Claims, 11 Drawing Sheets

(56) References Cited

OTHER PUBLICATIONS

Bivas-Benita et al., "Non-invasive pulmonary aerosol delivery in mice by the endotracheal route," *European Journal of Pharmaceutics and Biopharmaceutics*, vol. 61, pp. 214-218, 2005.
Eyles et al., "Analysis of local and systemic immunological responses after intra-tracheal, intra-nasal and intra-muscular administration of microsphere co-encapsulated *Yersinia pestis* sub-unit vaccines," *Vaccine*, vol. 16, No. 20, pp. 2000-2009, 1998.
Fujihashi et al., "A dilemma for mucosal vaccination: efficacy versus toxicity using enterotoxin-based adjuvants," *Vaccine*, vol. 20, pp. 2431-2438, 2002.
Griffiths et al., "Liposomally-encapsulated ricin toxoid vaccine delivered intratracheally elicits a good immune response and protects against a lethal pulmonary dose of ricin toxin," *Vaccine*, vol. 17/18, pp. 1933-1939, 1997.
Hogenesch et al.., "Systemic and pulmonary immune response to intrabronchial administration of ovalbumin in calves," *Veterinary Immunology and Immunopathology*, vol. 51, pp. 293-302, 1996.
Honko et al., "Flagellin is an Effective Adjuvant for Immunization against Lethal Respiratory Challenge with *Yersinia pestis," Infection and Immunity*, vol. 74, No. 2, pp. 1113-1120, Feb. 2006.
Hu et al., "The immunostimulating complex (ISCOM) is an efficient mucosal delivery system for respiratory syncytial virus (RSV) envelope antigens," *Clin. Exp. Immunol.*, vol. 113, pp. 235-243, 1998.
Lombry et al., "Local and Systemic Immune Responses to Intratracheal Instillation of Antigen and DNA Vaccines in Mice," *Pharmaceutical Research*, vol. 21, No. 1, pp. 127-135, Jan. 2004.
Lu et al., "Pulmonary vaccine delivery," *Expert Rev. Vaccines*, vol. 6, No. 2, pp. 213-226, 2007.
Lu et al., "Liposomal Dry Powders as Aerosols for Pulmonary Delivery of Proteins," *AAPS PharmSciTech*, vol. 6, No. 4, pp. E641-E648, 2005.
Maloy et al., "Induction of Th1 and Th2 CD4+ T cell responses by oral or parenteral immunization with ISCOMS," *Eur. J. Immunol.*, vol. 25, pp. 2835-2841, 1995.
McBride et al., "Systemic and pulmonary antibody responses of calves to *Pasteurella haemolytica* after intrapulmonary inoculation," *Am. J. Vet. Res.*, vol. 53, No. 10, pp. 1889-1894, Oct. 1992.
Menzel et al., "Inhalative vaccination with pneumococcal polysaccharide in healthy volunteers," *Vaccine*, vol. 23, pp. 5113-5119, 2005.
Meyer et al., "Inhalative vaccination with pneumococcal polysaccharide in patients with chronic obstructive pulmonary disease," *Vaccine*, vol. 24, pp. 5832-5838, 2006.
Nardelli-Haefliger et al., "Immune responses induced by lower airway mucosal immunization with a human papillomaviurs type 16 virus-like particle vaccine," *Vaccine*, vol. 23, pp. 3634-3641, 2005.
Nesburn et al., "Local and systemic B cell and Th1 responses induced following ocular mucosal delivery of multiple epitopes of herpes simplex virus type 1 glycoprotein D together with cytosine-phosphate-guanine adjuvant," *Vaccine*, vol. 23, pp. 873-883, 2005.
Orson et al., "Protection against influenza infection by cytokine-enhanced aerosol genetic immunization," *The Journal of Gene Medicine*, vol. 8, pp. 488-497, 2006.
Pabst et al., "A Single Intratracheal Dose of the Growth Factor Fms-Like Tyrosine Kinase Receptor-3 Ligand Induces a Rapid Differential Increase of Dendritic Cells and Lympocyte Subsets in Lung tissue and Bronchoalveolar Lavage, Resulting in an Increased Local Antibody Production," *The Journal of Immunology*, vol. 171, pp. 325-330, 2003.
Smith et al., "Evaluation of novel aerosol formulations designed for mucosal vaccination against influenza virus," *Vaccine*, vol. 21, pp. 2805-2812, 2003.
Stanley et al., "Intranasal immunisation with *Toxoplasma gondii* tachyzoite antigen encapsulated into PLG microspheres induces humoral and cell-mediated immunity in sheep," *Vaccine*, vol. 22, pp. 3929-3941, 2004.
Waldman et al., "An Evaluation of Influenza Immunization," *Bull. Wdl. Hlth. Ong.*, vol. 41, pp. 543-548, 1969.
Wigley et al., "Aerosol Immunization of Human with Tetnaus Toxoid," *The Journal of Immunology*, vol. 103, No. 5, pp. 1096-1098, Nov. 1969.
Zanvit et al., "Immune response after adjuvant mucosal immunization of mice with inactivated influenza virus," *Immunology Letters*, vol. 97, pp. 251-259, 2005.
International Search Report issued on Dec. 16, 2008 in application No. PCT/AU2008/001500 (corresponding to U.S. Appl. No. 12/679,654).
Office Action issued on Nov. 10, 2010 by the Examiner in U.S. Appl. No. 12/439,054 (US 2009/0324642).
Pearse et al., "ISCOMATRIX® adjuvant for antigen delivery," Advanced Drug Delivery Reviews, vol. 57, pp. 465-474, 2005.
Drane et al., "The ISCOMATRIX™ adjuvant," Immunopotentiators in Modern Vaccines, Chapter 12, pp. 191-215, 2006.
Sjölander et al., "Intranasal immunization with influenza-ISCOM induces strong mucosal as well as systemic antibody and cytotoxic T-lymphocyte responses," Vaccine, vol. 19, pp. 4072-4080, 2001.
De Haan et al., "Induction of a sceretory IgA response in the murine female urogenital tract by immunization of the lungs with liposome-supplemented viral subunit antigen," Vaccine, vol. 13, No. 7, pp. 613-616, 1995.
Marshall et al., "Antibodies to the Major Linear Neutralizing Domains of Cytomegalovirus Glycoprotein B Among Natural Seropositives and CMV Vaccine Recipients," Viral Immunology, vol. 13, No. 3, pp. 329-341, 2000.
Office Action issued on Aug. 23, 2013 in U.S. Appl. No. 12/439,054 (US 2009/0324642).
Office action dated Mar. 19, 2014 issued in connection with U.S. Appl. No. 12/439,054.

* cited by examiner

FIG. 1A

Amino Acid Alignment: Nucleoprotein (NP)

```
                           10         20         30         40         50         60         70         80
                            |          |          |          |          |          |          |          |
          Conserved:********** ***** **** ********** *  ****** ********** **********  ********* ****** ***
A/Puerto Rico/8/34   MASQGTKRSY EQMETDGERQ NATEIRASVG KMIGGIGRFY IQMCTELKLS DYEGRLIQNS LTIERMVLSA FDERRNKYLE
A/Indonesia/5/05     .......... .....G.... .......... R.VS...... .......... .......... I......... ......R...
A/Viet Nam/1194/2004.......... .....G.... .......... R.VS...... .......... .......... I......... ......R...

                           90        100        110        120        130        140        150        160
                            |          |          |          |          |          |          |          |
          Conserved:********** *********   *** ***** ********** ****** *** ***** **** ********** **********
A/Puerto Rico/8/34   EHPSAGKDPK KTGGPIYRRV NGKWMRELIL YDKEEIRRIW RQANNGDDAT AGLTHMMIWH SNLNDATYQR TRALVRTGMD
A/Indonesia/5/05     .......... .........R D...V..... .......... ......E... .....L.... .......... ..........
A/Viet Nam/1194/2004.......... .........R D...V..... .......... ......E... .....L.... .......... ..........

                          170        180        190        200        210        220        230        240
                            |          |          |          |          |          |          |          |
          Conserved:********** ********** ********** *** ****** ********** *** ****** ********** ***** ****
A/Puerto Rico/8/34   PRMCSLMQGS TLPRRSGAAG AAVKGVGTMV MELVRMIKRG INDRNFWRGE NGRKTRIAYE RMCNILKGKF QTAAQKAMMD
A/Indonesia/5/05     .......... .......... .......... ...I...... .......... ...R...... .......... .....R....
A/Viet Nam/1194/2004.......... .......... .......... ...I...... .......... ...R...... .......... .....R....

                          250        260        270        280        290        300        310        320
                            |          |          |          |          |          |          |          |
          Conserved:********** ** *** *** ********** ********** ** ******* ********** ********** ** *******
A/Puerto Rico/8/34   QVRESRNPGN AEFEDLTFLA RSALILRGSV AHKSCLPACV YGPAVASGYD FEREGYSLVG IDPFRLLQNS QVYSLIRPNE
A/Indonesia/5/05     .......... ..I...I... .......... .......... ..L....... .......... .......... ..F.......
A/Viet Nam/1194/2004.......... ..I...I... .......... .......... ..L....... .......... .......... ..F.......
```

FIG. 1A - CONTINUED

```
                         330        340        350        360        370        380        390        400
                           |          |          |          |          |          |          |          |
          Conserved:********** ********** *** *** **  * *** *** ********** ** * * *** ********** *********
A/Puerto Rico/8/34   NPAHKSQLVW MACHSAAFED LRVLSFIKGT KVLPRGKLST RGVQIASNEN METMESSTLE LRSRYWAIRT RSGGNTNQQR
A/Indonesia/5/05     .......... .......... ...S..R.. R.V...Q... .......... ..V.D.N... .......... .........K
A/Viet Nam/1194/2004.......... .......... ...S..R.. R.V...Q... .......... ..A.D.N... .......... ..........

                         410        420        430        440        450        460        470        480
                           |          |          |          |          |          |          |          |
          Conserved:******* ** **********  * ******  ********** ********** ********** ********** *  *******
A/Puerto Rico/8/34   ASAGQISIQP TFSVQRNLPF DRTTIMAAFN GNTEGRTSDM RTEIIRMMES ARPEDVSFQG RGVFELSDEK AASPIVPSFD
A/Indonesia/5/05     .......V.. .......... E.A.....T .......... .......... .......... .......... .TN.......
A/Viet Nam/1194/2004.......V.. .......... E.A.....T .......... .......... .......... .......... .TN.......

                              490        500
                                |          |
          Conserved:   * ******** *****
A/Puerto Rico/8/34     MSNEGSYFFG DNAEEYDNx
A/Indonesia/5/05       .N........ .........
A/Viet Nam/1194/2004   .N........ .....----
```

FIG. 1B

```
                             10        20        30        40        50        60        70        80
                              |         |         |         |         |         |         |         |
          Conserved:********** ********** ****** *** ********** ********* ********** ********** **********
A/Puerto Rico/8/34   MSLLTEVETY VLSIIPSGPL KAEIAQRLED VFAGKNTDLE VLMEWLKTRP ILSPLTKGIL GFVFTLTVPS ERCLQRRRFV
A/Indonesia/5/2005   .......... .......... ......K... .......... A......... .......... .......... ..........
A/Viet Nam/1194/2004.......... .......... ......K... .......... A......... .......... .......... ..........

                             90       100       110       120       130       140       150       160
                              |         |         |         |         |         |         |         |
          Conserved:********** **** ***** ********* ****  **** .********* ****** *** ********** **********
A/Puerto Rico/8/34   QNALNGNGDP NNMDKAVKLY RKLKREITFH GAKEISLSYS AGALASCMGL IYNRMGAVTT EVAFGLVCAT CEQIADSQHR
A/Indonesia/5/2005   .......... ....R..... K......... ....V..... T......... ....T..... .......... ..........
A/Viet Nam/1194/2004.......... ....R..... K......... ....VA.... T......... ....T..... .......... ..........

                            170       180       190       200       210       220       230       240
                              |         |         |         |         |         |         |         |
          Conserved:***** * ** ********** ********** ********** **** * *** ********** *** *****    ********
A/Puerto Rico/8/34   SHRQMVTTTN PLIRHENRMV LASTTAKAME QMAGSSEQAA EAMEVASQAR QMVQAMRTIG THPSSSAGLK NDLLENLQAY
A/Indonesia/5/2005   .....A.I.. .......... .......... .......... ......N... .......... ...N.....R DN........
A/Viet Nam/1194/2004.....A.I.. .......... .......... .......... ....I.N... .......... ...N.....R DN........

                            250       260       270       280       290       300       310       320
                              |         |         |         |         |         |         |         |
          Conserved:  ********** ***
A/Puerto Rico/8/34    QKRMGVQMQR FKx
A/Indonesia/5/2005    .......... ...
A/Viet Nam/1194/2004 .......... ...
```

Figure 2
(A)
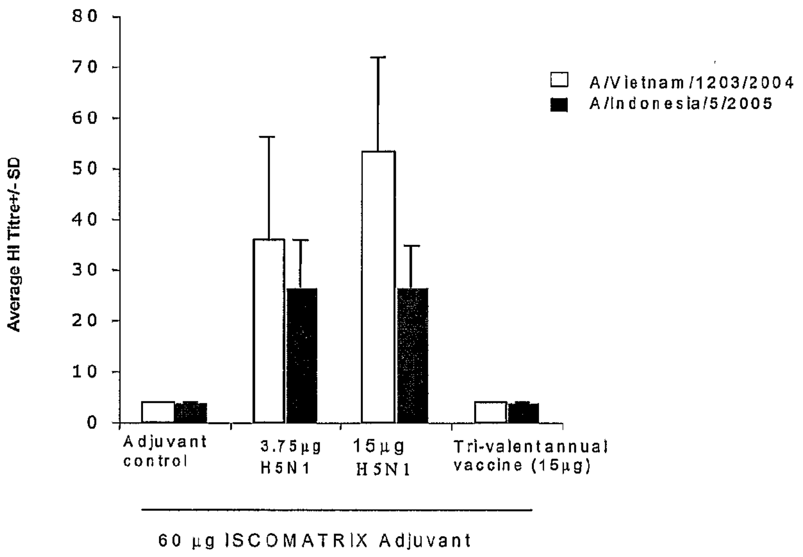
(B)
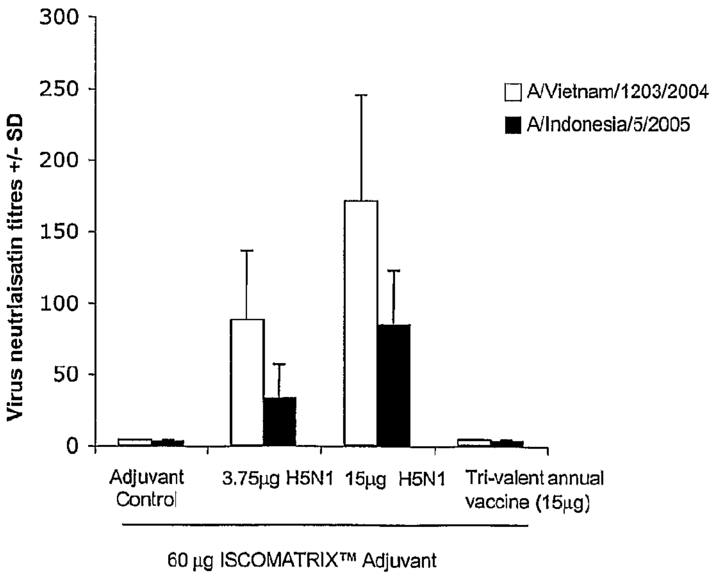

i) ISCOMATRIX™ adjuvant alone (control)

FIG. 3B - CONTINUED
ii) 3.75µg H5N1 + ISCOMATRIX™ adjuvant
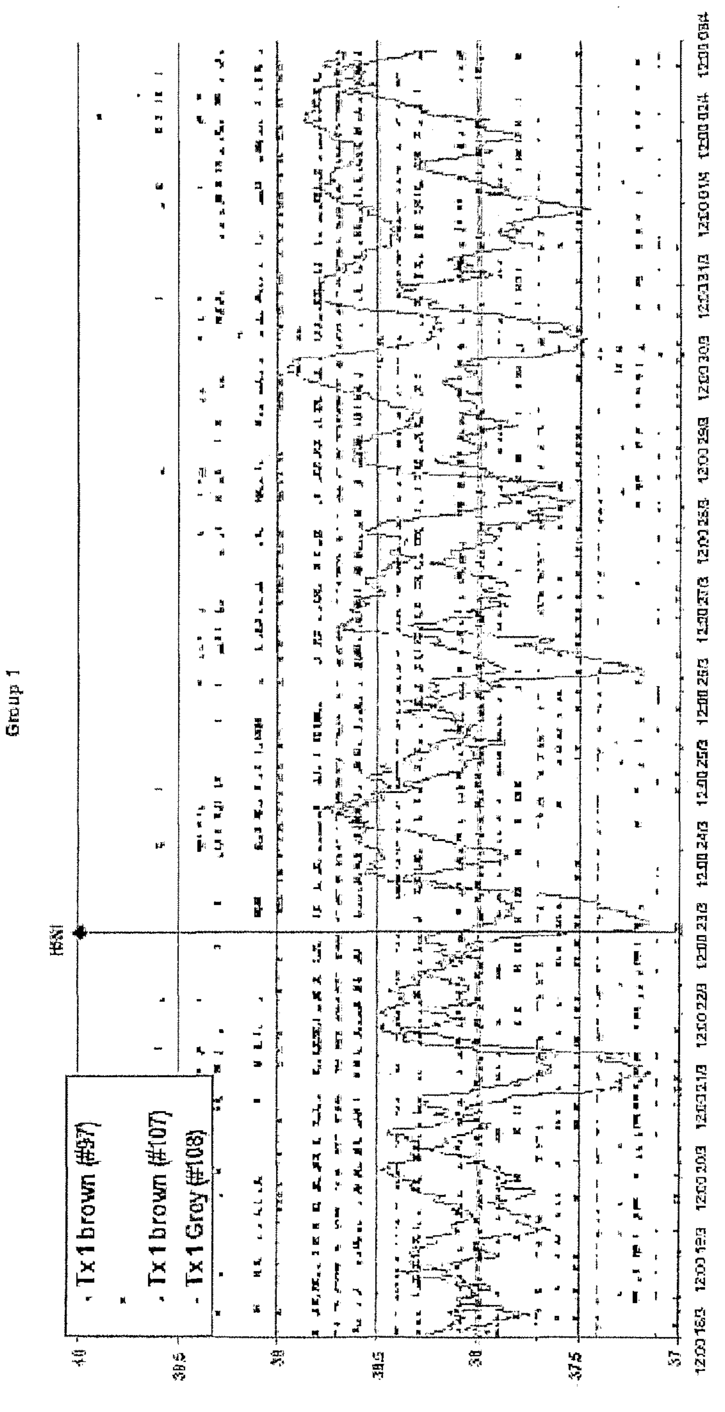

FIG. 3B - CONTINUED
iii) 15µg H5N1 + ISCOMATRIX™ adjuvant
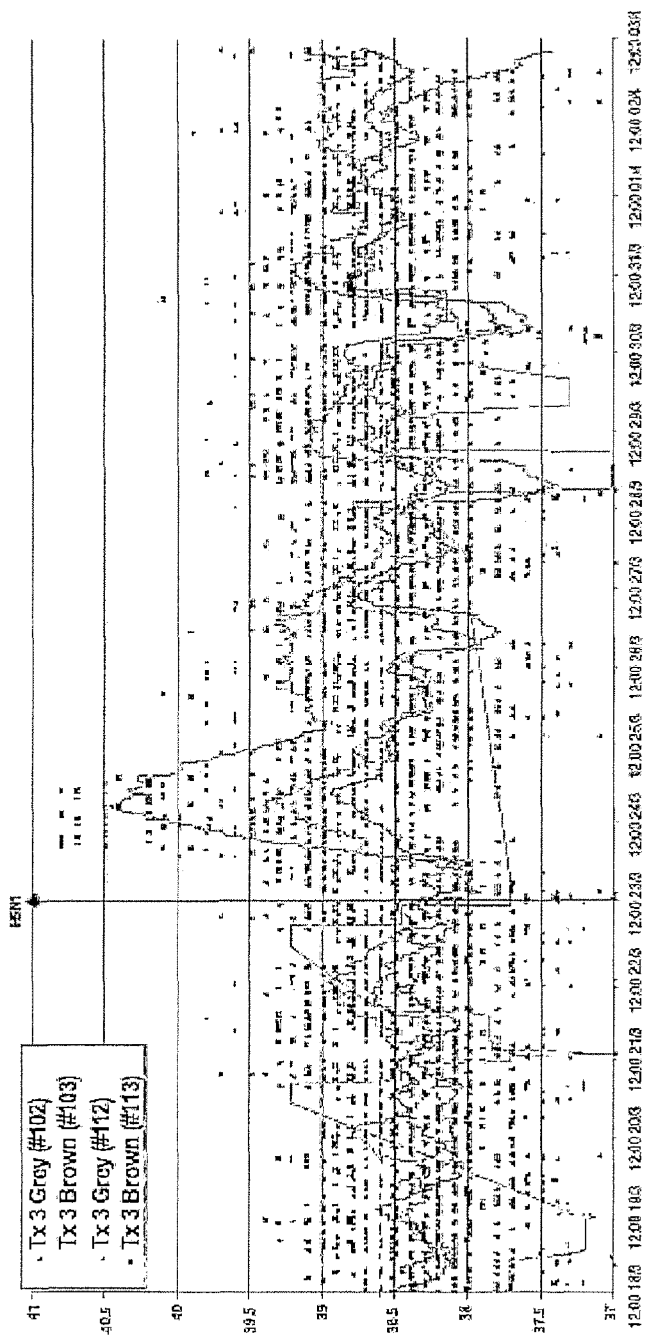

FIG. 3B - CONTINUED
iv) Influenza ISCOMATRIX™ vaccine.
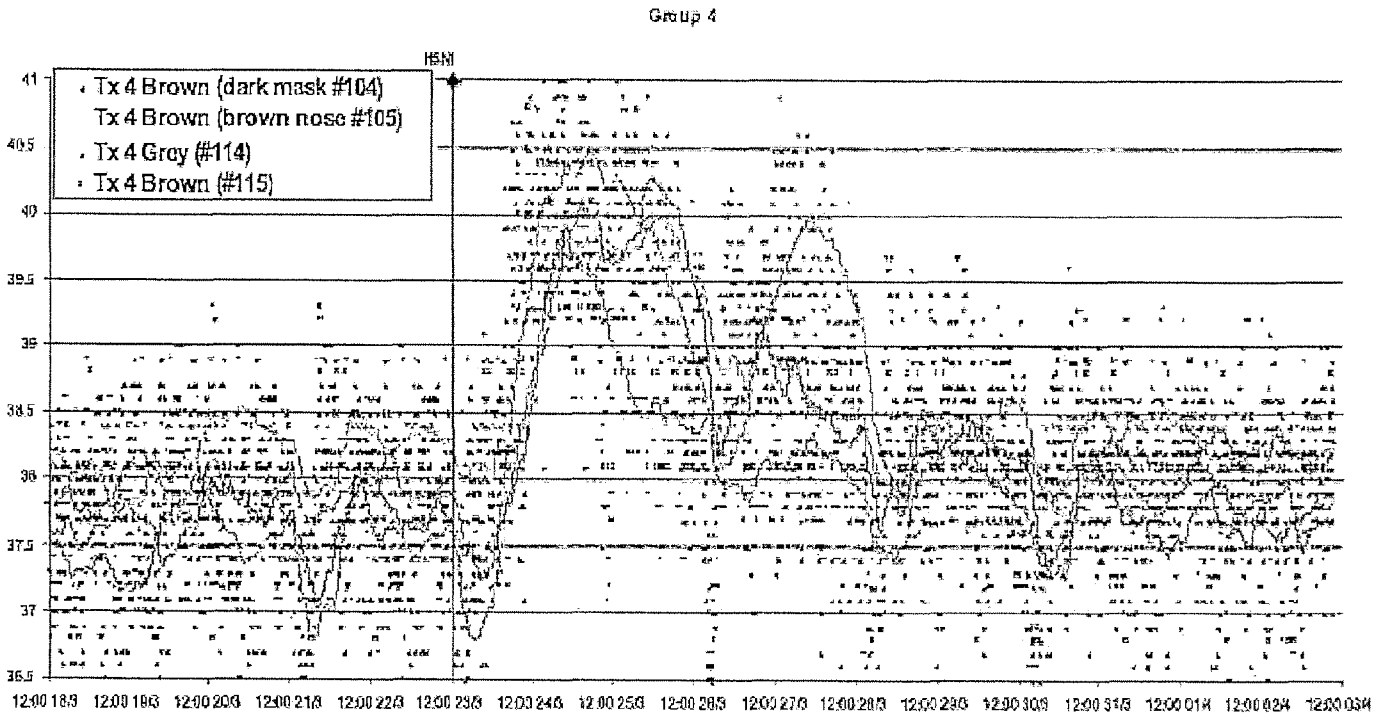

SEQUENCE LISTING

<160> NUMBER OF SEQ ID NOS: 6

<210> SEQ ID NO 1
<211> LENGTH: 499
<212> TYPE: PRT
<213> ORGANISM: Influenza A virus
<220> FEATURE:
<221> NAME/KEY: MOD_RES
<222> LOCATION: (499)..(499)
<223> OTHER INFORMATION: Any amino acid

<400> SEQUENCE: 1

Met Ala Ser Gln Gly Thr Lys Arg Ser Tyr Glu Gln Met Glu Thr Asp
1 5 10 15

Gly Glu Arg Gln Asn Ala Thr Glu Ile Arg Ala Ser Val Gly Lys Met
20 25 30

Ile Gly Gly Ile Gly Arg Phe Tyr Ile Gln Met Cys Thr Glu Leu Lys
35 40 45

Leu Ser Asp Tyr Glu Gly Arg Leu Ile Gln Asn Ser Leu Thr Ile Glu
50 55 60

Arg Met Val Leu Ser Ala Phe Asp Glu Arg Arg Asn Lys Tyr Leu Glu
65 70 75 80

Glu His Pro Ser Ala Gly Lys Asp Pro Lys Lys Thr Gly Gly Pro Ile
85 90 95

Tyr Arg Arg Val Asn Gly Lys Trp Met Arg Glu Leu Ile Leu Tyr Asp
100 105 110

Lys Glu Glu Ile Arg Arg Ile Trp Arg Gln Ala Asn Asn Gly Asp Asp
115 120 125

Ala Thr Ala Gly Leu Thr His Met Met Ile Trp His Ser Asn Leu Asn
130 135 140

Asp Ala Thr Tyr Gln Arg Thr Arg Ala Leu Val Arg Thr Gly Met Asp
145 150 155 160

Pro Arg Met Cys Ser Leu Met Gln Gly Ser Thr Leu Pro Arg Arg Ser
165 170 175

Gly Ala Ala Gly Ala Ala Val Lys Gly Val Gly Thr Met Val Met Glu
180 185 190

Leu Val Arg Met Ile Lys Arg Gly Ile Asn Asp Arg Asn Phe Trp Arg
195 200 205

Gly Glu Asn Gly Arg Lys Thr Arg Ile Ala Tyr Glu Arg Met Cys Asn
210 215 220

Ile Leu Lys Gly Lys Phe Gln Thr Ala Ala Gln Lys Ala Met Met Asp
225 230 235 240

Gln Val Arg Glu Ser Arg Asn Pro Gly Asn Ala Glu Phe Glu Asp Leu
245 250 255

Thr Phe Leu Ala Arg Ser Ala Leu Ile Leu Arg Gly Ser Val Ala His
260 265 270

Lys Ser Cys Leu Pro Ala Cys Val Tyr Gly Pro Ala Val Ala Ser Gly
275 280 285

Tyr Asp Phe Glu Arg Glu Gly Tyr Ser Leu Val Gly Ile Asp Pro Phe
290 295 300

Arg Leu Leu Gln Asn Ser Gln Val Tyr Ser Leu Ile Arg Pro Asn Glu
305 310 315 320

Asn Pro Ala His Lys Ser Gln Leu Val Trp Met Ala Cys His Ser Ala
325 330 335

Ala Phe Glu Asp Leu Arg Val Leu Ser Phe Ile Lys Gly Thr Lys Val
340 345 350

```
Leu Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Asn Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn Xaa


<210> SEQ ID NO 2
<211> LENGTH: 499
<212> TYPE: PRT
<213> ORGANISM: Influenza A virus
<220> FEATURE:
<221> NAME/KEY: MOD_RES
<222> LOCATION: (499)..(499)
<223> OTHER INFORMATION: Any amino acid

<400> SEQUENCE: 2

Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
            20                  25                  30

Val Ser Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Arg Tyr Leu Glu
65                  70                  75                  80

Glu His Pro Ser Ala Gly Lys Asp Pro Lys Lys Thr Gly Gly Pro Ile
                85                  90                  95

Tyr Arg Arg Arg Asp Gly Lys Trp Val Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
```

```
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Val Pro Arg Gly Gln Leu Ser Thr Arg Gly Val Gln Ile Ala Ser Asn
        355                 360                 365

Glu Asn Met Glu Val Met Asp Ser Asn Thr Leu Glu Leu Arg Ser Arg
    370                 375                 380

Tyr Trp Ala Ile Arg Thr Arg Ser Gly Gly Asn Thr Asn Gln Gln Lys
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Asn Asn Glu Gly Ser Tyr Phe Phe Gly Asp Asn Ala Glu Glu Tyr
                485                 490                 495

Asp Asn Xaa


<210> SEQ ID NO 3
<211> LENGTH: 495
<212> TYPE: PRT
<213> ORGANISM: Influenza A virus

<400> SEQUENCE: 3

Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
            20                  25                  30

Val Ser Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Arg Tyr Leu Glu
```

-continued

```
65                  70                  75                  80

Glu His Pro Ser Ala Gly Lys Asp Pro Lys Lys Thr Gly Gly Pro Ile
                85                  90                  95

Tyr Arg Arg Arg Asp Gly Lys Trp Val Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Val Pro Arg Gly Gln Leu Ser Thr Arg Gly Val Gln Ile Ala Ser Asn
        355                 360                 365

Glu Asn Met Glu Ala Met Asp Ser Asn Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Asn Asn Glu Gly Ser Tyr Phe Phe Gly Asp Asn Ala Glu Glu
                485                 490                 495
```

<210> SEQ ID NO 4
<211> LENGTH: 253
<212> TYPE: PRT
<213> ORGANISM: Influenza A virus
<220> FEATURE:
<221> NAME/KEY: MOD_RES
<222> LOCATION: (253)..(253)
<223> OTHER INFORMATION: Any amino acid

<400> SEQUENCE: 4

```
Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys Xaa
                245                 250
```

<210> SEQ ID NO 5
<211> LENGTH: 253
<212> TYPE: PRT
<213> ORGANISM: Influenza A virus
<220> FEATURE:
<221> NAME/KEY: MOD_RES
<222> LOCATION: (253)..(253)
<223> OTHER INFORMATION: Any amino acid

<400> SEQUENCE: 5

```
Met Ser Leu Leu Thr Glu Val Glu Thr Tyr Val Leu Ser Ile Ile Pro
1               5                   10                  15

Ser Gly Pro Leu Lys Ala Glu Ile Ala Gln Lys Leu Glu Asp Val Phe
            20                  25                  30
```

```
Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
            100                 105                 110

Lys Glu Val Ser Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Ala Thr Ile Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Asn Gln
        195                 200                 205

Ala Arg Gln Met Val Gln Ala Met Arg Thr Ile Gly Thr His Pro Asn
    210                 215                 220

Ser Ser Ala Gly Leu Arg Asp Asn Leu Leu Glu Asn Leu Gln Ala Tyr
225                 230                 235                 240

Gln Lys Arg Met Gly Val Gln Met Gln Arg Phe Lys Xaa
                245                 250


<210> SEQ ID NO 6
<211> LENGTH: 253
<212> TYPE: PRT
<213> ORGANISM: Influenza A virus
<220> FEATURE:
<221> NAME/KEY: MOD_RES
<222> LOCATION: (253)..(253)
<223> OTHER INFORMATION: Any amino acid

<400> SEQUENCE: 6

Met Ser Leu Leu Thr Glu Val Glu Thr Tyr Val Leu Ser Ile Ile Pro
1               5                   10                  15

Ser Gly Pro Leu Lys Ala Glu Ile Ala Gln Lys Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
```

-continued

```
    130                 135                 140

Gly Leu Val Cys Ala Thr Cys Glu Gln Ile Ala Asp Ser Gln His Arg
145                 150                 155                 160

Ser His Arg Gln Met Ala Thr Ile Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Ile Ala Asn Gln
        195                 200                 205

Ala Arg Gln Met Val Gln Ala Met Arg Thr Ile Gly Thr His Pro Asn
    210                 215                 220

Ser Ser Ala Gly Leu Arg Asp Asn Leu Leu Glu Asn Leu Gln Ala Tyr
225                 230                 235                 240

Gln Lys Arg Met Gly Val Gln Met Gln Arg Phe Lys Xaa
                245                 250
```

METHOD OF ELICITING AN IMMUNE RESPONSE AGAINST PANDEMIC INFLUENZA VIRUS

FIELD OF THE INVENTION

This invention relates to a method of eliciting or inducing an immune response in a subject against pandemic subtypes of influenza virus, and more particularly to a method of eliciting or inducing an immune response in the subject which protects the subject against subsequent challenge with a pathogenic, pandemic subtype of influenza A, such as the avian influenza A (H5N1) that has caused infections in humans.

BACKGROUND OF THE INVENTION

Influenza is a major cause of disease in humans and a source of significant morbidity and mortality worldwide with large segments of the human population affected every year. Influenza viruses can be subtyped into A, B and C. The majority of viruses that circulate in the human population are influenza A and B.

Annual vaccination is the primary strategy for preventing infections. The A strain of influenza can be further subtyped, based on the antigenic differences of the two viral surface transmembrane proteins, Haemagglutinin (HA) and Neuraminidase (NA). To date 16 HA (HA1-16) and 9 NA (NA1-9) glycoprotein subtypes of influenza A viruses have been identified. At present, two subtypes of influenza A circulate in humans (H1N1 and H3N2) [1].

On occasion, an influenza pandemic can occur when a new influenza virus emerges for which people have little or no immunity. In the past century, three influenza A strain pandemic outbreaks have caused significant human influenza-related fatalities (1918, H1N1; 1957, H2N2; 1968, H3N2) [2]. In Hong Kong in 1997, a highly pathogenic H5N1 avian influenza virus was transmitted directly from chickens to humans, causing six deaths from 18 confirmed infections [3;4]. Since this time, concern regarding an influenza pandemic has been heightened by sporadic outbreaks of pathogenic H5N1 viruses. These outbreaks have resulted in 258 cases with 153 deaths across six countries, with outbreaks from Asia through to Europe (Cambodia, China, Indonesia, Thailand, Turkey, and Vietnam) [5].

Since 1997, viruses of several other subtypes, including H2N2, H9N2, H7N7, H7N3 and H10N7, have also been implicated in human infections and consequently these subtypes also represent a significant pandemic threat. Because it is not possible to predict which subtype of influenza virus will cause the next pandemic, an ideal vaccine would protect the host from severe disease or death by eliciting an immune response that protects the host against a broad range of influenza viruses, from the same or different subtypes. However, for the reasons outlined below, the available vaccines, which rely on the induction of a neutralising antibody response (primarily against HA and NA), are highly influenza strain-specific.

The HA and NA glycoproteins of influenza viruses undergo antigenic variation as a means to escape the host immune response [6]. The presence of virus neutralising antibodies specific for the HA glycoprotein at systemic or mucosal sites protects against infection with influenza. However, as a consequence of antigenic variability the antibody response to HA is highly strain-specific, and does not recognise the HA from influenza viruses of different subtypes, or even highly divergent strains within the same subtype [7].

Cell-mediated immunity on the other hand, in particular $CD8^+$cytotoxic T cells ($CD8^+$CTL) is primarily responsible for clearing virus-infected cells, and thus limits the severity of, and promotes recovery from infection [8]. In contrast to HA, the internal protein targets of the cell-mediated immune response—the key ones being PB2, PA, Nucleoprotein (NP) and Matrix protein (M)—are not prone to antigenic drift and as a consequence are highly conserved. For example, the NP and M proteins of the H5N1 strains A/Indonesia/5/05 and A/Vietnam/1194/04 share approximately 94% amino acid identity with A/Puerto Rico/8/34 (as shown in FIG. 1). A/Puerto/Rico/8/34 is an H1N1 virus isolated in 1934, and the source of the structural proteins for the engineered vaccine strains, traditionally prepared by re-assortment and more recently by reverse genetics. Furthermore, there is a high degree of conservation of CTL epitopes between these different influenza subtypes. Extension of this analysis to include other virus subtypes, including H7N7 and H9N2, which also pose a potential pandemic threat, demonstrates a high degree of conservation of CTL epitopes across all A-strain viruses. Therefore, unlike the HA antibody response which is highly strain-specific, CTL responses have the potential to be broadly effective, irrespective of the influenza A-strain subtype [9]. Therefore, the ability to induce a strong CTL response is a highly desirable feature for a pandemic influenza vaccine.

The induction of $CD8^+$ CTL, particularly in humans, has to date proven to be a significant hurdle for vaccine development. Delivery systems such as DNA and viral vectors have offered some hope, but have potential safety concerns, and in the case of DNA, generally elicit poor cellular responses, in particular $CD8^+$ CTL responses. Additionally, viral vectors have the problem of inducing neutralising antibodies to the vector, which limits repeated use. Prime-boost combinations of DNA and live viral vector delivery are currently being evaluated, and although results have been promising in animal models, they are yet to be proven in humans. ISCOM™ vaccines have been shown in numerous animal models, to be potent inducers of both T-helper ($CD4^+$) and CTL ($CD8^+$) T cell responses to a wide variety of antigens, including naturally occurring immunogens and recombinant proteins [10]. An H1N1 influenza ISCOM™ vaccine has been shown to confer cross protection in mice against lethal challenge with heterologous viruses, including H2N2, H3N2, H5N1 and H9N2 viruses [11]. Furthermore, protection was shown to be dependent on both $CD8^+$ T cells and antibody [11].

It is generally accepted that the ability of ISCOM™ vaccines to induce strong $CD8^+$ CTL responses is largely due to the fact that the antigen is incorporated into the ISCOM™ particle [12], which results in efficient cellular uptake and subsequent access of the antigen to the MHC Class I processing machinery [13]. However, the manufacture of ISCOM™ vaccines is complex, difficult to scale up, and there are significant problems associated with manufacturing control and consistency. Therefore ISCOM™ vaccines, despite demonstrating protection against a range of pathogens in a wide variety of animal species, have limited product potential, particularly for high volume products such as pandemic influenza vaccine which would demand the production of hundreds of millions of doses in a short time frame.

In work leading to the present invention, the inventors have developed a vaccine formulation in which preformed ISCOMATRIX™ adjuvant which is "immunogen-free" in that it has essentially the same composition and structure as the ISCOM™ vaccine but without the incorporated antigen[12; 14], is combined or mixed with influenza immunogen(s) such as the standard tri-valent seasonal influenza vaccine as described below. Thus, in contrast to ISCOM™ vaccines, the influenza immunogen(s) in the vaccine formulation of the present invention are not incorporated into the ISCOMATRIX™ adjuvant structure. Accordingly, the production of the vaccine formulations of the present invention is simple, robust and reproducible, and can be performed at a large scale.

Furthermore, the work leading to the present invention has demonstrated the ability of the vaccine formulation comprising standard endemic influenza immunogen(s) to protect against lethal challenge with a highly pathogenic, pandemic (H5N1) subtype of influenza A virus, using ferrets as an animal model.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

SUMMARY OF THE INVENTION

The present invention provides a method for eliciting or inducing a protective immune response in a subject against a pandemic subtype of influenza virus, which comprises administering to the subject a composition comprising (i) at least one immunogen of an endemic influenza subtype, and
(ii) an immunogen-free immunostimulating complex as adjuvant.

In another aspect, the present invention provides the use of a composition comprising (i) at least one immunogen of an endemic influenza subtype, and
(ii) an immunogen-free immunostimulating complex as adjuvant, in the manufacture of a medicament for administration to a subject to elicit or induce a protective immune response in the subject against a pandemic subtype of influenza virus.

In yet another aspect, the invention provides the use of a composition comprising (i) at least one immunogen of an endemic influenza subtype, and
(ii) an immunogen-free immunostimulating complex as adjuvant, to elicit or induce a protective immune response in a subject against a pandemic subtype of influenza virus.

In a further aspect, the invention provides an agent for eliciting or inducing a protective immune response in a subject against a pandemic subtype of influenza virus, wherein said agent is a composition comprising (i) at least one immunogen of an endemic influenza subtype, and
(ii) an immunogen-free immunostimulating complex as adjuvant.

BRIEF DESCRIPTION OF THE DRAWINGS

FIG. 1 is an amino acid sequence comparison of (A) Nucleoprotein (NP), and (B) Matrix protein (M) from A/Puerto Rico/8/34 (H1N1), A/Indonesia/5/05 (H5N1) and A/Vietnam/1194/04 (H5N1) (SEQ ID NO: 1-6). The bolded letters are the described human CTL epitopes (adapted from Suzanne L. Epstein, Jonathan W. Yewdell, Jack R. Bennink, available on the world wide web at flu.lanl.gov/review/epitopes.html) The NP & M proteins of A/Indonesia/5/05 and A/Vietnam/1194/04 share approximately 93% amino acid identity with A/Puerto Rico/8/34.

FIG. 2 shows HI antibody (A) and Virus Neutralisation titres (B) of sera from ferrets inoculated with either (i) tri-valent seasonal influenza vaccine (containing 15 μg of A/New Caledonia/20/99, A/Wisconsin/67/2005 and B/Malaysia/2506/2004) combined with ISCOMATRIX™ adjuvant (60 μg); (ii) A/Vietnam/1194/2004 combined with ISCOMATRIX™ adjuvant (60 μg); or (iii) ISCOMATRIX™ adjuvant alone (adjuvant control). Sera was collected at day 28 after second vaccination and titrated against ANietnam/1203/2004 and A/Indonesia/5/2005. Data are presented as the average of four animals per group. Standard deviation is indicated.

FIG. 3 shows survival (A), change in body temperature (B), and change in weight (C) of ferrets challenged with $10^6$ 50% egg infectious dose ($ED_{50}$) of A/Vietnam/1203/2004 following immunization with either, (i) tri-valent seasonal influenza vaccine (containing 15 μg of A/New Caledonia/20/99, A/Wisconsin/67/2005 and B/Malaysia/2506/2004) combined with ISCOMATRIX™ adjuvant (60 μg); (ii) A/Vietnam/1194/2004 combined with ISCOMATRIX™ adjuvant (60 μg) or (iii) ISCOMATRIX™ adjuvant alone (adjuvant control) as indicated. Data are representative values of the four animals per group.

DETAILED DESCRIPTION OF THE INVENTION

Figure 3A:
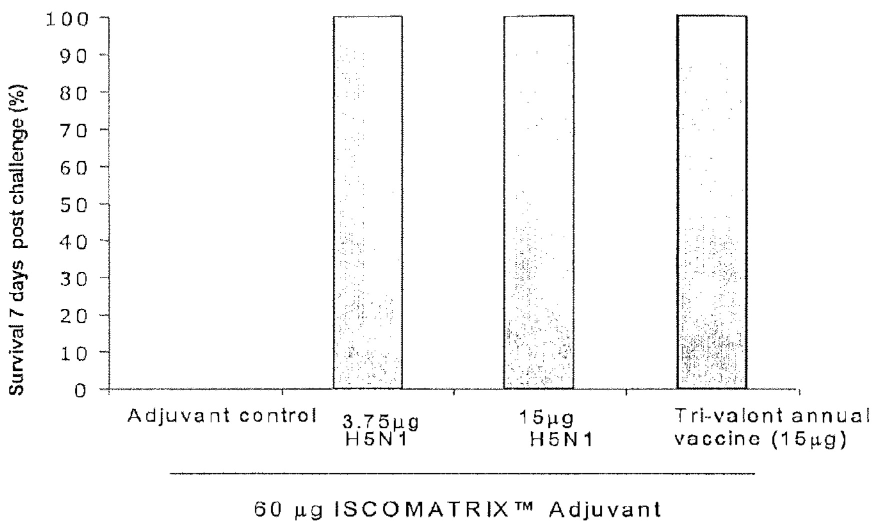
In FIG. 3A, post viral challenge ferrets were weighed and examined physically daily. Ferrets that had lost more than 10% of body weight or showed signs of distress such as tremor or abdominal discomfort were euthanized for ethical reasons.

In one aspect, the present invention provides a method for eliciting or inducing a protective immune response in a subject against a pandemic subtype of influenza virus, which comprises administering to the subject a composition comprising (i) at least one immunogen of an endemic influenza subtype, and
(ii) an immunogen-free immunostimulating complex as adjuvant.

Preferably, the subject is a human. However, the method of the invention also extends to eliciting or inducing a protective immune response in a non-human animal or bird subject such as a livestock animal or bird, a laboratory test animal or bird, a companion animal or bird, or a wild animal or bird.

In accordance with the invention, the composition administered to the subject comprises at least one immunogen of an endemic influenza subtype. As noted above, the "endemic" influenza A subtypes presently circulating in humans are the H1N1 and H3N2 subtypes. Accordingly, the composition of the invention preferably comprises humunogen(s) of one or both of these subtypes. In one particular embodiment of the present invention, the composition may comprise a standard tri-valent influenza vaccine comprising inactivated endemic influenza virus types A (H1N1 and H3N2) and B, such as the Fluvax® split virion, inactivated influenza vaccine (CSL Limited, Melbourne, Australia).

As used herein, references to "pandemic" subtypes of influenza virus are to be understood as references to subtypes to which the subject population, particularly the human population, is considered to be naïve, that is to have no or little resistance either as a result of prior vaccination or prior exposure. As noted above, such pandemic subtypes include in particular, the H5N1, H2N2, H9N2, H7N7, H7N3 and H10N7 subtypes.

Administration of the composition comprising immunogen(s) of endemic influenza subtypes in accordance with the present invention has been shown to elicit or induce a heterologous protective immune response against a pandemic subtype of influenza virus.

As used herein, references to "an immune response" are to be understood as broadly referring to both a humoral response (such as induction of virus neutralizing antibodies) and a cell-mediated immune response (such as induction of $CD8^+$ cytotoxic T cells). References herein to "a protective immune response" include an immune response which protects the subject from subsequent infection, or reduces the likelihood of subsequent infection, upon challenge or exposure to the pandemic subtype of influenza virus, and includes amelioration of the symptoms of any subsequent infection as well as reduction of the severity of any subsequent infection.

The composition administered to the subject in accordance with the present invention includes an immunogen-free immunostimulating complex as adjuvant, which is combined or mixed with the influenza immunogen(s). As used herein, the term "immunogen-free" means that the immunostimulating complex is formed without any immunogen or antigen being incorporated into the structure of the complex. Preferably, this adjuvant is a saponin-based immunogen-free immunostimulating complex comprising saponin, a sterol (such as cholesterol), and optionally a phospholipid (such as phosphatidylethanolamine or phosphatidylcholine), formed as typically rigid, hollow, spherical, cage-like particles measuring about 40 nm in diameter, and known as "empty ISCOMs", ISCOM matrix, or more recently as ISCOMATRIX™ adjuvant [23]. Most preferably, the immunogen-free immunostimulating complex is ISCOMATRIX™ adjuvant.

Conventional pharmaceutically acceptable carriers, excipients, buffers or diluents, may be included in compositions of this invention. Generally, a composition in accordance with the present invention will comprise an immunologically effective amount of the influenza immunogen(s) admixed with the adjuvant, in conjunction with one or more conventional pharmaceutically acceptable carriers and/or diluents. As used herein "pharmaceutically acceptable carriers and/or diluents" include any and all solvents, dispersion media, aqueous solutions, coatings, antibacterial and antifungal agents, isotonic and absorption delaying agents and the like. The use of such media and agents for pharmaceutical active substances is well known in the art and is described by way of example in *Remington's Pharmaceutical Sciences*, $18^{th}$ Edition, Mack Publishing Company, Pennsylvania, U.S.A.

The influenza immunogen(s) included in the composition of the present invention are administered in an effective amount. An "effective amount" means an amount necessary at least partly to attain the desired immune response, in particular the desired protective immune response. The amount varies depending upon the age, health and physical condition of the individual to be treated, the racial background of the individual to be treated, the degree of protection desired, the formulation of the composition, the assessment of the medical situation, and other relevant factors. It is expected that the amount will fall in a relatively broad range that can be determined through routine trials. If necessary, the administration of an effective amount may be repeated one or several times. The actual amount administered will be determined both by the nature of the desired protective immune response and by the rate at which the active immunogen is being administered.

In accordance with the present invention, the composition is preferably administered to the subject by a parenteral route of administration. Parenteral administration includes any route of administration that is not through the alimentary canal (that is, not enteral), including administration by injection, infusion and the like. Administration by injection includes, by way of example, into a vein (intravenous), an artery (intraarterial), a muscle (intramuscular) and under the skin (subcutaneous). The composition is preferably administered subcutaneously, intradermally or intramuscularly, in a dosage which is sufficient to obtain the desired immune response.

Compositions suitable for parenteral administration conveniently comprise a sterile aqueous preparation of the active component which is preferably isotonic with the blood of the recipient. This aqueous preparation may be formulated according to known methods using suitable dispersing or wetting agents and suspending agents. The sterile injectable preparation may also be a sterile injectable solution or suspension in a non-toxic parenterally-acceptable diluent or solvent, for example as a solution in a polyethylene glycol and lactic acid. Among the acceptable vehicles and solvents that may be employed are water, Ringer's solution, suitable carbohydrates (e.g. sucrose, maltose, trehalose, glucose) and isotonic sodium chloride solution. In addition, sterile, fixed oils are conveniently employed as a solvent or suspending medium. For this purpose, any bland fixed oil may be employed including synthetic mono- or di-glycerides. In addition, fatty acids such as oleic acid find use in the preparation of injectables.

The present invention also provides the use of a composition comprising (i) at least one immunogen of an endemic influenza subtype, and (ii) an immunogen-free immunostimulating complex as adjuvant, in the manufacture of a medicament for administration to a subject to elicit or induce a protective immune response in the subject against a pandemic subtype of influenza virus.

The invention further provides the use of a composition comprising (i) at least one immunogen of an endemic influenza subtype, and (ii) an immunogen-free immunostimulating complex as adjuvant, to elicit or induce a protective immune response in a subject against a pandemic subtype of influenza virus.

In addition, the invention provides an agent for eliciting or inducing a protective immune response in a subject against a pandemic subtype of influenza virus, wherein said agent is a composition comprising (i) at least one immunogen of an endemic influenza subtype, and (ii) an immunogen-free immunostimulating complex as adjuvant.

In accordance with the present invention, it has been shown that immunization with standard tri-valent seasonal influenza vaccine containing A/New Caledonia/20/99 (H1N1), A/Wisconsin/67/2005 (H3N2) and B/Malaysia/2506/2005 admixed with immunogen-free ISCOMATRIX™ adjuvant (referred to herein as "Influenza ISCOMATRIX™ Vaccine") affords protection against lethal challenge with wildtype A/Vietnam/1203/04 (H5N1).

Influenza ISCOM™ vaccines have been shown to induce a $CD8^+$ CTL response in a variety of species including humans [10;15;16]. However, to date there are no reports of ISCOMATRIX™-containing vaccines providing protection against lethal challenge in any animal models. Because the antigen in an ISCOMATRIX™ vaccine is simply mixed with and not incorporated into the ISCOMATRIX™ adjuvant structure, the induction of $CD8^+$CTL responses is generally believed to be less efficient than with an ISCOM™ vaccine containing the same amount of incorporated antigen [12;17-20].

For this reason, a range of strategies have been developed to associate proteins with preformulated ISCOMATRIX™ adjuvant to produce associated ISCOMATRIX™ vaccines. These include methods that take advantage of the physical properties of the ISCOMATRIX™ adjuvant such as electrostatic interactions, where positively charged proteins will associate with the negatively charged adjuvant. Procedures for modifying either the protein or the adjuvant to maximise this type of association have also been developed [21]. Other methods for achieving association include modifications of the components of the ISCOMATRIX™ adjuvant to enable coupling of proteins to various exposed chemical groups. One example of this type of modification is referred to as chelating ISCOMATRIX™ adjuvant, in which a metal chelating group is incorporated into the structure, which can then bind proteins containing a metal affinity tag such as hexahistidine [18].

Therefore, given the expected requirement for the antigen to be incorporated into the ISCOMATRIX™ adjuvant (as in an ISCOM™ vaccine) for optimal induction of cellular immune responses, it is highly surprising that immunisation of ferrets with Influenza ISCOMATRIX™ Vaccine (standard tri-valent seasonal influenza vaccine containing A/New Caledonia/20/99 (H1N1), A/Wisconsin/67/2005 (H3N2), and B/Malaysia/2506/2004 simply admixed with immunogen-free ISCOMATRIX™ adjuvant) protected against lethal challenge with wildtype ANietnam/1203/04 (H5N1). Further, this protection was observed in the absence of a detectable neutralising antibody response to H5N1, indicating that the cellular immune responses (most probably $CD8^+$ CTLs) induced by the Influenza ISCOMATRIX™ Vaccine are capable of protecting a naïve animal from severe disease and death following lethal challenge with a highly pathogenic H5N1 influenza virus.

The ferret has been the experimental animal of choice for many virologists who are interested in studying human influenza. The ferret has been particularly useful to study: (i) pathogenesis of influenza including H5N1 isolates; (ii) response to challenge infection after vaccination; (iii) efficacy of antivirals; (iv) transmissibility of antiviral drug-resistant mutants; (v) viral shedding and (vi) the febrile response to influenza. The alternate model is the mouse, and the wealth of different genetically modified mouse strains and the large range of readily available reagents for analysis of the immune response have made this a compelling model and a great deal has been learnt from its use. However, mice are not naturally infected by human influenza viruses and there are no known influenza viruses of mice. This natural resistance may be due to the presence of the Mx gene, which confers type 1 interferon-dependent protection against influenza (in mice but not humans), and also due to the presence of unique inhibitors of the virus in murine secretions [22]. Influenza viruses suitable for growth in mice are limited and those that are routinely used have been "mouse-adapted" by blind passage in this host. In contrast, ferrets are naturally susceptible to human influenza so there is no restriction on the viral strains that can be studied.

Further features of the present invention are more fully described in the following Example. It is to be understood, however, that this detailed description is included solely for the purposes of exemplifying the present invention, and should not be understood in any way as a restriction on the broad scope of the invention as set out above.

EXAMPLE

A. Materials and Methods

Ferrets: Juvenile female or male ferrets (3-5 month old), approximately 700-1500 g in weight were sourced from IMVS (SA). Ferrets were seronegative to currently circulating influenza (H1N1, H3N2, B viruses). Blood samples were collected immediately prior to each vaccination and prior to viral challenge. A further blood sample to check the antibody response to challenge was taken 14 days after exposure to virus or at the time of euthanasia. Bleeds were performed on anaesthetised (Ketamine/Medetomidine 50:50 0.1 ml/kg, reversed with Apitemazole) animals from the jugular or axillary veins, 4 sites, 1 ml each, using 19 to 23 gauge needle depending on the size of the ferret. Clinically affected animals were euthanased immediately following either a 10% body weight loss or exhibition of signs consistent with involvement of other organ systems eg. tremor, or abdominal discomfort.

Vaccine: The mixture of seasonal influenza antigen used for injection included equal amounts (15 μg) of A/New Caledonia/20/99 (H1N1), A/Wisconsin/67/2005 (H3N2) and B/Malaysia/2506/2004 (CSL Limited, Melbourne, Australia). For pandemic strains, monovalent antigen (A/Vietnam/1194/2004) was prepared in an identical manner to seasonal strains. In brief, virus was propagated in embryonated eggs, inactivated with β-propiolactone (ICN Pharmaceuticals Inc., Costa Mesa, Calif.), subjected to zonal centrifugation on a sucrose gradient, and treated with sodium taurodeoxycholate (Sigma, St. Louis, Mich.) to yield a purified, inactivated and disrupted antigen preparation. The concentration of viral antigen was expressed in terms of haemagglutinin (HA) protein, which was determined by standard single radial immunodiffusion and compared to a known standard of the relevant strain. ISCOMATRIX™ adjuvant in PBS pH 6.2[23] was added to the influenza antigen immediately prior to dosing.

Vaccine dosing: Two 0.5 ml doses (21 days apart) delivered intramuscularly into the quadriceps or posterior muscle of the hind legs, using a 1 ml syringe with a 27 gauge needle.

Viruses: The H5N1 human influenza viruses: A/Vietnam/1203/04 (wild-type) A/Vietnam/1194/04 (reverse engineered vaccine strain), and A/Indonesia/5/2005 (wild-type) were obtained from World Health Organisation Influenza Collaborating Laboratories. Stock viruses were propagated in the allantoic cavity of 10-day-old embryonated chicken eggs at 35° C. for 24-36 hr and stored at −70° C. All experiments with highly pathogenic viruses were conducted in a BSL 3+ containment facility (AAHL, CSIRO Geelong).

Viral challenge: Three weeks post Dose 2, the ferrets were inoculated intra-nasally (both nostrils) with $10^6$ 50% egg infectious dose ($EID_{50}$) of wild-type challenge virus (ANietnam/1203/2004) as described by Govorkova et al [24].

Immunogenicity Tests: Immunogenicity was assessed by haemagglutination inhibition (HI), and virus neutralisation (VN) (as described in the WHO Collaborating Centre for Influenza, Standard Operating Procedures) using two-fold dilutions of serum and a single stock source of HA antigen. Geometric mean titres were determined and seroprotection defined as a 4-fold or greater rise in antibody titre above the pre-vaccination titre. Statistical significance of viral titre and morbidity data was determined using a two-tailed, paired Student's t-test. Statistical significance of mortality data was determined by Chi squared analysis.

Clinical Assessment:

Observations: Animals were visually monitored daily throughout the study and twice daily following challenge if the animals show signs of disease. General clinical observations were made prior to challenge with specific records kept of any respiratory symptoms such as coughing or sneezing. Reaction site observations (i.e. erythema, oedema) were noted at 2, 24 and 48 hrs following each vaccination. Following challenge, activity scores were monitored daily.

Weight: Animals were weighed while under sedation at the time of dosing and challenge (Day 0) and Days 3, 5, 7 and 14 post-challenge.

Temperature: Temperature was determined manually at sedation using digital thermometers and continuously using a temperature transponder inserted subcutaneously with the aid of a 22 gauge needle approximately ten days prior to viral challenge.

Biological Samples: Nasal, oral swabs were taken on Days 3, 5 and 7 post-challenge for virus isolation.

B. Results

Influenza ISCOMATRIXT™ Vaccine: Antibody Responses

Prior to the commencement of the ferret immunogenicity and challenge studies, sera was collected from the ferrets and tested by Enzyme Linked Immunoassay (ELISA), using standard methodology for the presence of antibodies to A/New Caledonia/20/1999 (H1N1), A/Wisconsin/67/2005 (H3N2) and B/Malaysia/2506/2004. All ferrets tested were negative for antibodies against all 3 strains, and were therefore considered as naive for influenza.

For the immunogenicity and challenge studies, ferrets were immunised twice (days 0, 21), with 3.75 μg or 15 μs of HA from A/Vietnam/1194/2004 admixed with ISCOMATRIX™ adjuvant (60 μg), or the current seasonal tri-valent influenza vaccine, containing 15 μg of HA from each of A/New Caledonia/20/1999 (H1N1), A/Wisconsin/67/2005 (H3N2) and B/Malaysia/2506/2004 admixed with ISCOMATRIX™ adjuvant (60 μm) (referred to as Influenza ISCOMATRIX™ Vaccine). A group of control animals was similarly dosed with ISCOMATRIX™ adjuvant alone. Sera collected 28 days post the second dose was assessed for the presence of influenza-specific antibody using haemagglutination inhibition (HI) (FIG. 1A) and viral neutralisation (VN) (FIG. 1B) assays. As shown in FIG. 2, ferrets immunised with the A/Vietnam/1194/2004 ISCOMATRIX™ vaccine at both antigen doses (3.75 μg & 15 μg) elicited strong antibody responses to both A/Vietnam/1203/2004 (H5N1, Glade 1) and A/Indonesia/5/2005 (H5N1, Glade 2), demonstrating that despite being from different H5N1 clades, A/Vietnam/1203/2004 and A/Indonesia/5/2005 are antigenically and serologically closely related.

In contrast, sera from the ferrets that were immunised with the Influenza ISCOMATRIX™ Vaccine were negative by HI and VN against both A/Vietnam/1203/2004 and A/Indonesia/5/2005. As expected, control ferrets that received 2 doses of ISCOMATRIX® adjuvant alone were also negative in both assays.

Influenza ISCOMATRIX™ Vaccine: Protection against lethal challenge

Four weeks post the $2^{nd}$ vaccine dose, ferrets were inoculated intra-nasally (both nostrils) with $10^6$ 50% egg infectious dose ($EID_{50}$) of challenge virus (A/Vietnam/1203/2004) as described by Govorkova et al [24]. The ferrets were then monitored continuously for temperature and daily for weight, physical appearance and morbidity.

As shown in FIG. 3A, all of the animals that had been immunised with the A/Vietnam/1994/2004 ISCOMATRIX™ vaccines at both HA antigen levels (3.75 μg & 15 μm) survived lethal challenge with wild-type (AJVietnam/1203/2004) virus. This result is not surprising, given that these animals developed high titre A/Vietnam/1203/2004-specific antibody in response to these vaccines, as shown in FIG. 2. Surprisingly, however, the ferrets that had been immunised with the Influenza ISCOMATRIX™ Vaccine also survived lethal challenge, despite the absence of detectable neutralising antibody. As expected, all of the control ferrets succumbed to the viral challenge and had to be euthanased for ethical reasons either because they had lost more than 10% body weight or showed signs of distress such as tremor or abdominal discomfort.

Figure 3B:
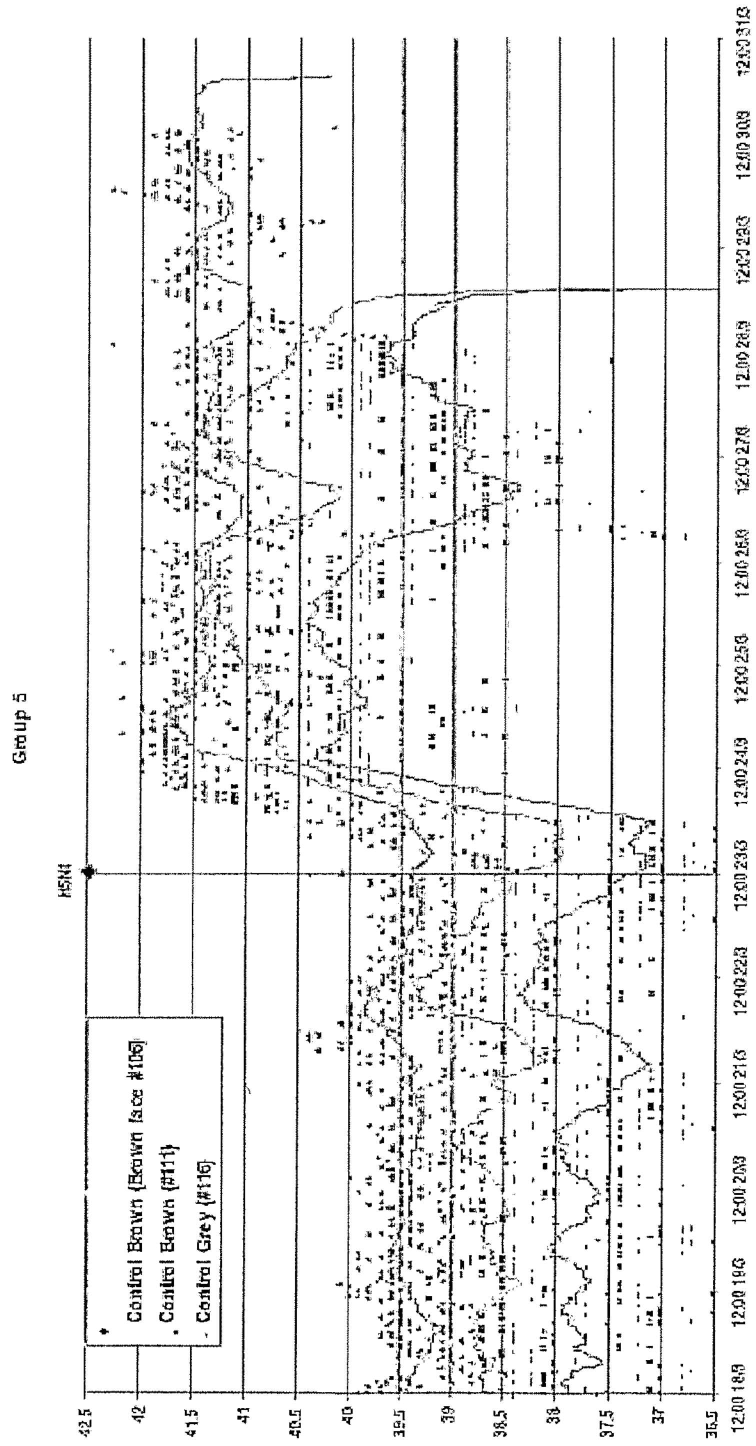
In FIG. 3B, ferret temperature was monitored daily by use of a subcutaneous implantable temperature transponder. The vertical line represents time of challenge. The mean body temperature of an uninfected ferret is 38.8° C. Data are representative values of the four animals per group.

The temperature of the ferrets was monitored continuously using a subcutaneous temperature transponder for 3 days pre-challenge to establish the base line and then for a further 7 days post-challenge. As shown in FIG. 3B, the temperature of the control ferrets rose sharply by 2.5-3.0° C.12-24 hrs post-challenge and remained at this elevated level until they were euthanased for ethical reasons. Similarly, the temperature of ferrets immunised with the Influenza ISCOMATRIX™ Vaccine rose sharply by 2.5-3.0° C.12-24 hrs post-challenge, however this rise was transient and temperatures returned to baseline 24 hrs later. One animal in this group experienced a $2^{nd}$ slightly lower transient spike in temperature, which again returned to baseline 24 hrs later. In contrast, with the exception of one animal in the high antigen dose group, the post-challenge temperature of all ferrets immunised with an A/Vietnam/1994/2004 ISCOMATRIX™ vaccine did not at any stage rise above the pre-challenge baseline level.

Figure 3C:
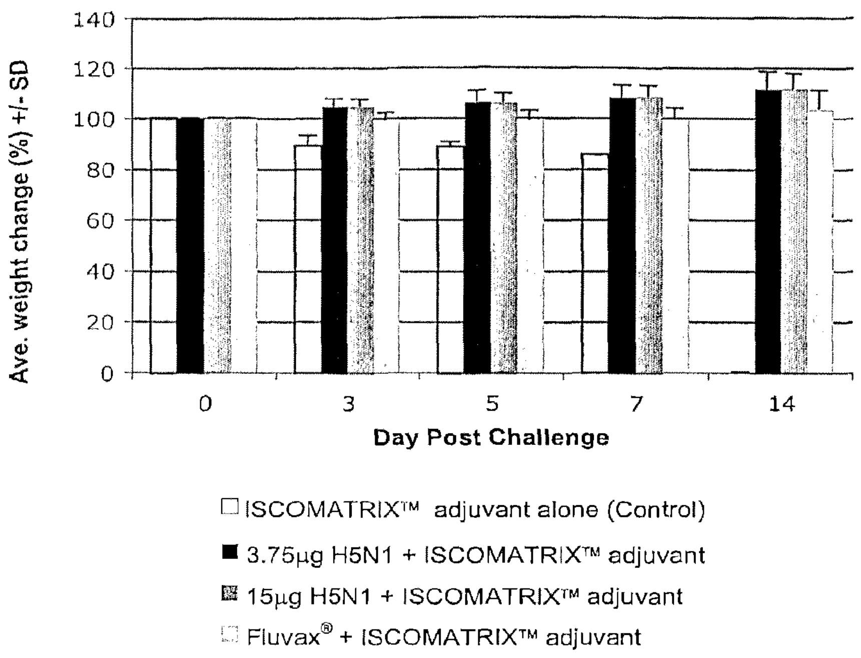
In FIG. 3C, ferret weights are represented as the percentage of the weight of the animal at the time of challenge. Data are representative values of the four animals per group.

The weight of the ferrets was monitored daily throughout the study period (FIG. 3C). The weight of all animals in the control group dropped by approximately 10% within 3 days of challenge. Consistent with the static temperature profiles of the ferrets immunised with the A/Vietnam/1994/2004 ISCOMATRIX™ vaccines, the weight of these animals increased steadily post-challenge. In contrast, the weight of the ferrets immunised with the Influenza ISCOMATRIX™ Vaccine remained unchanged throughout the 7 day post-challenge observation period.

Figure 4:
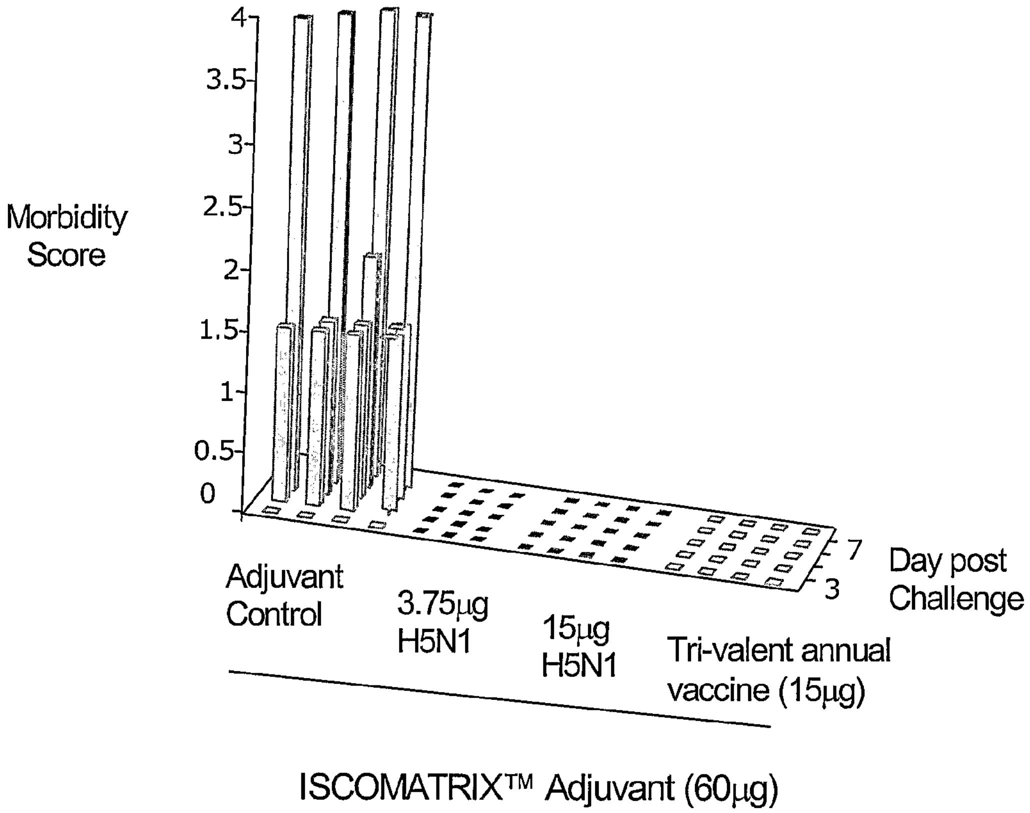
FIG. 4 shows morbidity scores obtained with ferrets immunised with either: (i) tri-valent seasonal influenza vaccine (containing 15 μg of A/New Caledonia/20/99, A/Wisconsin/67/2005 and B/Malaysia/2506/2004) combined with ISCOMATRIX™ adjuvant (60 μg); (ii) A/Vietnam/1194/2004 combined with ISCOMATRIX™ adjuvant (60 μg); or (iii) ISCOMATRIX™ adjuvant alone (adjuvant control) as indicated. Following challenge with $10^6$ 50% egg infectious dose ($EID_{50}$) of A/Vietnam/1203/2004, ferrets were monitored for behavior and given a morbidity score based on the following scale (0=playful and alert, 1=alert but playful only when induced to play, 2=alert but not playful when stimulated, 3=neither alert or playful, 4=exhibiting physical symptoms necessitating euthanasia, as described Materials & Methods.

Consistent with the weight and temperature data, all ferrets immunised with A/Vietnam/1994/2004 ISCOMATRIX™ vaccine at both antigen levels (3.75 μm or 15 μg HA) or the Influenza ISCOMATRIX™ Vaccine remained playful and alert post lethal challenge with wild-type H5N1 virus (A/Vietnam/1203/2004). In contrast, control animals that received ISCOMATRIX™ adjuvant alone demonstrated signs of morbidity, and by day 3 post-challenge were neither playful or alert, and by day 5-7 their physical condition had deteriorated to a level that necessitated euthanasia (FIG. 4).

C. Discussion

The key and surprising observation made during study is that the Influenza ISCOMATRIX™ Vaccine, containing 15 µg of HA from each of A/New Caledonia/20/1999 (H1N1), A/Wisconsin/67/2005 (H3N2) and B/Malaysia/2506/2004 combined with ISCOMATRIX™ adjuvant protected ferrets against lethal challenge with a highly pathogenic H5N1 virus (A/Vietnam/1203/2004) in the absence of a detectable neutralising antibody response (HI and VN) to A/Vietnam/1203/2004. The transient rise in temperature of ferrets in the Influenza ISCOMATRIX™ Vaccine group suggests that following challenge these animals became infected, but that the extent of viral infection was limited by non-neutralising-antibody-mediated immunological mechanisms leading to rapid clearance of the virus and recovery from infection.

The observation that these animals did not lose weight and remained active and alert post challenge supports this conclusion. In contrast, the control animals that received 2 doses of ISCOMATRIX™ adjuvant alone experienced a rapid, prolonged temperature rise and their health status deteriorated rapidly to a point that necessitated euthanasia.

At present, due to absence of assays to evaluate ferret cellular immune responses, in particular $CD8^+$ CTL responses, it is not possible to identify the immunological basis for protection afforded by the Influenza ISCOMATRIX™ Vaccine against lethal challenge with an H5N1 virus. Influenza ISCOM™ vaccines have been shown to induce $CD8^+$ CTL responses in a variety of species including humans [10;15;16]. Furthermore, an H1N1 ISCOM™ vaccine has been shown in mice to protect against heterologous challenge in part due to the induction of a cross-protective $CD8^+$ CTL response. However, as mentioned above, it is widely accepted that the induction of optimal $CD8^+$ CTL responses requires the antigen to be incorporated into the ISCOM™ or ISCOMATR1x™ adjuvant [17-19]. It is therefore surprising to observe in this study that in the absence of a detectable neutralising antibody response, the Influenza ISCOMATRIX™ Vaccine induced a cellular immune response, most likely although not formally proven a $CD8^+$ CTL response, that was potent enough to protect ferrets against lethal challenge with a highly pathogenic H5N1 virus. Furthermore, given the high degree of sequence conservation between the internal proteins (including the identified $CD8^+$ CTL epitopes) of all A-strain influenza viruses, it is reasonable to assume that the Influenza ISCOMATRIX™ Vaccine would similarly protect against other potential pandemic strains, including but not limited to: H7N7, H7N3, H9N2 and H10N7.

References

[1] Lin Y P, Gregory V, Bennett M, Hay A. Recent changes among human influenza viruses. Virus Res 2004 July; 103 (1-2):47-52.

[2] Oxford J S. Influenza A pandemics of the 20th century with special reference to 1918: virology, pathology and epidemiology. Rev Med Virol 2000 March; 10(2):119-33.

[3] Subbarao K, Klimov A, Katz J, et al. Characterization of an avian influenza A (H5N1) virus isolated from a child with a fatal respiratory illness. Science 1998 Jan. 16; 279 (5349):393-6.

[4] Claas E C, Osterhaus A D, van B R, et al. Human influenza A H5N1 virus related to a highly pathogenic avian influenza virus. Lancet 1998 Feb. 14; 351(9101):472-7.

[5] World Health Organization. Cumulative Number of Confirmed Human cases of Avian Influenza A/(H5N1) Reported to WHO. 2006. Ref Type: Data File

[6] Potter C W, Oxford J S. Determinants of immunity to influenza infection in man. Br Med Bull 1979; 35: 69-75.

[7] Nozaki Y, Hasegawa Y, Takeuchi A, et al. Nitric oxide as an inflammatory mediator of radiation pneumonitis in rats. Am J Physiol 1997; 272(4 Pt 1):L651-L658.

[8] Epstein S L, Lo C Y, Misplon J A, Bennink J R. Mechanism of protective immunity against influenza virus infection in mice without antibodies. J Immunol 1998; 160:322-7.

[9] Ulmer J B, Donnelly J J, Parker S E, et al. Heterologous protection against influenza by injection of DNA encoding a viral protein. Science 1993; 259(5102):1745-9.

[10] Sjölander A, Drane D, Maraskovsky E, et al. Immune responses to ISCOM formulations in animal and primate models. Vaccine 2001; 19(17-19):2661-5.

[11] Sambhara S, Kurichh A, Miranda R, et al. Heterosubtypic immunity against human influenza A viruses, including recently emerged avian H5 and H9 viruses, induced by FLU-ISCOM vaccine in mice requires both cytotoxic T-lymphocyte and macrophage function. Cell Immunol 2001 Aug. 1; 211(2):143-53.

[12] Morein B. The iscom antigen-presenting system. Nature 1988; 332(6161):287-8.

[13] Villacres M C, Behboudi S, Nikkila T, Lövgren-Bengtsson K, Morein B. Internalization of iscom-borne antigens and presentation under MHC class I or class II restriction. Cell Immunol 1998; 185(1):30-8.

[14] Lövgren K, Morein B. The requirement of lipids for the formation of immunostimulating complexes (iscoms). Biotechnol Appl Biochem 1988; 10(2):161-72.

[15] Ennis F A, Cruz J, Jameson J, Klein M, Burt D, Thipphawong J. Augmentation of human influenza A virus-specified cytotoxic T lymphocyte memory by influenza vaccine and adjuvanted carriers (ISCOMS). Virology 1999; 259(2):256-61.

[16] Rimmelzwaan G F, Nieuwkoop N, Brandenburg A, et al. A randomized, double blind study in young healthy adults comparing cell mediated and humoral immune responses induced by influenza ISCOM vaccines and conventional vaccines. Vaccine 2000; 19(9-10):1180-7.

[17] Cox J, Coulter A. Adjuvants—a classification and review of their modes of actions. Vaccine 1997; 15(3):248-56.

[18] Malliaros J, Quinn C, Arnold F H, et al. Association of antigens to ISCOMATRIX adjuvant using metal chelation leads to improved CTL responses. Vaccine 2004; 22(29-30):3968-75.

[19] Lenarczyk A, Le T T, Drane D, et al. ISCOM based vaccines for cancer immunotherapy. Vaccine 2004; 22(8): 963-74.

[20] Lövgren-Bengtsson K, Sjölander A. Adjuvant activity of iscoms; effect of ratio and co-incorporation of antigen and adjuvant. Vaccine 1996; 14(8):753-60.

[21] Le T T T, Drane D, Malliaros J, et al. Cytotoxic T cell polyepitope vaccines delivered by ISCOMs. Vaccine 2001; 19(32):4669-75.

[22] Horisberger M A. Interferons, Mx genes, and resistance to influenza virus. Am J Respir Crit Care Med 1995; 152 (Suppl.):S67-S71.

[23] Drane D, Pearse M. The ISCOMATRIX adjuvant. In: Schijns VE, O'Hagan D T, editors. Immunopotentiators in modern vaccines.Amsterdam; Boston, Elsevier Academic Press, 2006: p. 191-216.

[24] Govorkova E A, Rehg J E, Krauss S, et al. Lethality to ferrets of H5N1 influenza viruses isolated from humans and poultry in 2004. J Virol 2005 February; 79(4):2191-8.

The invention claimed is:

1. A method for eliciting or inducing a protective immune response in a subject in need of protection against a pandemic subtype of influenza virus, which comprises administering to the subject a composition comprising (i) at least one immunogen of an endemic influenza subtype, and (ii) an immunogen-free immunostimulating complex as adjuvant, in an amount effective to elicit or induce a protective immune response against a pandemic subtype of influenza virus.

2. The method according to claim 1, wherein the subject is a human.

3. The method according to claim 1, wherein the composition comprises immunogen(s) of endemic influenza A HIN1 and/or H3N2 subtypes.

4. The method according to claim 1, wherein the immunogen-free immunostimulating complex comprises saponin, a sterol and optionally a phospholipid.

5. The method according to claim 4, wherein the immunogen-free immunostimulating complex comprises saponin, a sterol and a phospholipid.

6. The method according to claim 1, wherein the pandemic subtype of influenza virus is selected from the group consisting of influenza A H5N1, H7N7, H7N3, H9N2 and H10N7 subtypes.

7. The method according to claim 6, wherein the pandemic subtype is the influenza A H5N1 subtype.

* * * * *